United States Patent [19]

Yomoto et al.

[11] 3,998,696

[45] Dec. 21, 1976

[54] METHOD FOR PRODUCING MALTOSE

[75] Inventors: Chobe Yomoto; Takashi Adachi, both of Kawasaki; Yutaka Nakajima, Machida; Hidemasa Hidaka, Yokohama; Tsukasa Yoshida; Fumio Sugawara, both of Chiba, all of Japan

[73] Assignee: Meiji Seika Kaisha Ltd., Japan

[22] Filed: May 17, 1974

[21] Appl. No.: 471,137

[30] Foreign Application Priority Data

May 22, 1973 Japan ............................. 48-56373

[52] U.S. Cl. ............................. 195/31 R; 195/111
[51] Int. Cl.$^2$ ....................................... C12D 13/02
[58] Field of Search ................. 195/31 R, 66 R, 65, 195/11, 7, 111

[56] References Cited

UNITED STATES PATENTS

| | | | |
|---|---|---|---|
| 2,891,869 | 6/1959 | Langlois | 195/31 R |
| 3,549,496 | 12/1970 | Armbruster et al. | 195/31 R |
| 3,804,717 | 4/1974 | Koaze et al. | 195/65 |

FOREIGN PATENTS OR APPLICATIONS

| | | | |
|---|---|---|---|
| 1,232,645 | 5/1971 | United Kingdom | 195/31 R |

OTHER PUBLICATIONS

Chemical Abstracts, vol. 72, 41717u (1970).

*Primary Examiner*—A. Louis Monacell
*Assistant Examiner*—Thomas G. Wiseman
*Attorney, Agent, or Firm*—McGlew and Tuttle

[57] ABSTRACT

A method for producing a substance highly containing high content of maltose therein, by saccharifying a liquefied starch with amylase produced by streptomyces at the same time with or after treatment with β-amylase.

17 Claims, No Drawings

METHOD FOR PRODUCING MALTOSE

BACKGROUND OF THE INVENTION

1. Field of the Invention

The present invention relates to a method of producing maltose, wherein a liquefied starch is saccharified by an amylase produced by a strain of streptomyces and a β-amylase. Maltose is a disaccharide in which two molecules of D-glucose are combined with each other by α-linkage, being white powder or crystal extremely soluble in water, having delicious sweetness the degree of which is ½ to ⅓ that of sucrose.

Maltose is used as a sweetening agent having characteristics with which sucrose is not endowed sucrose and; also maltose can be used in various fields such as for a culture medium in the fermentation industries and a material for producing derivatives such as maltitol and the like.

2. Prior Art

Conventionally, β-amylase and isoamylase and/or pullulanase have been employed as indispensable enzymes and β-amylase has been used generally in the liquefying process in the industrial production of maltose enzymatically. Maltose and maltotriose are mainly contained in the substance which is produced by the combined action of these enzymes, and the yield of the maltotriose is influenced by the extent of the action of α-amylase. Maltotriose can not or can hardly hydrolyzed practically, as is well known, by any one of the foregoing three enzymes. It is required, therefore, for obtaining a substance with a higher content of maltose, to lessen the amount of maltotriose produced, as far as possible in the production by the enzymatic saccharization method. Indeed, when saccharification of starch was carried out by using a combination of α-amylase and β-amylase, the content of maltose in the product at most amounted to 40 to 70%. In order to obtain a higher yield of maltose, a liquefied starch having markedly low dextrose equivalent has been prepared by controlling the action of α-amylase in the liquefying process of the starch or by mechanically liquefying the starch, and the resultant liquefied starch has been saccharized by, e.g., β-amylase and isoamylase. The liquefied starch with low dextrose equivalent, however, is apt to retrograde, and the higher the concentration the greater the degree of retrogradation. The production of the substance containing a high content of maltose can not be easily carried out in a higher concentration of starch and usually, it may preferably be carried out under such an industrially disadvantageous condition as a low concentration of starch.

Furthermore, because of the low thermal stability of the isoamylase which has been commonly used in the industrial process, saccharifying temperature is at most in the range 50° to 55° C for the saccharification method using a combination of β-amylase and isoamylase, and this is liable to cause a high possibility of contamination in the saccharification process; therefore, such a method employing these enzymes is disadvantageous in an industrial process.

THE BRIEF DESCRIPTION OF THE INVENTION

The present invention relates to a method for producing a substance containing a high content of maltose therein, by which all of the disadvantages, as described above, in the conventional method are overcome, saccharifying a liquefied starch by β-amylase and an amylase which is produced by streptomyces (see French Pat. No. 71-38545).

More particularly, the present invention provides a new method on an industrial scale for producing maltose, which is far more advantageous than the conventional method; that is, the invention provides a method which is performed by a smaller amount of enzyme with a high concentration of starch in a shorter time for saccharification.

The present invention was accomplished as a result of the discovery that the substance containing a high content of maltose can be obtained from starch by utilizing a new amylase produced by particular strains of streptomyces and regarded as a kind of α-amylase by its properties, in combination with β-amylase under a specific condition. It had been also discovered that the streptomyces, or the amylase produced by streptomyces used in the present invention has a maltose productivity and liquefying ability with respect to starch, and if these abilities have been organically combined with that of β-amylase a, synergistic effect can be observed.

A streptomyces amylase may be added simultaneously with or subsequently to β-amylase in the saccharifying process.

A process for obtaining the amylase, produced by streptomyces and employed in the present invention, and some characteristics of the enzyme are described in the French Pat. No. 71-38545, an outline of which is as follows:

The particular strains of streptomyces which are used for the production of the amylase are shown below in detail.

| Strain | F.R.I. deposit No. | ATCC deposit No. |
|---|---|---|
| *Streptomyces tosaensis* SF-1085 (this strain was first isolated from soil and discovered by the present inventors) | 601 | 21723 |
| *Streptomyces hygroscopicus* SF-1084 (this strain is coincident with *Streptomyces hygroscopicus* as described in Waksman's "The Actinomycetes" vol. 2(1961) and in the Applied Microbiology, 10, 258–263 (1962)) | 602 | 21722 |
| *Streptomyces viridochromogenes* SF-1087 (this strain is coincident with *Streptomyces viridochromogenes* as described in Waksman's "The Actinomycetes" vol.2 (1961) and in the J. Bacteriol., 85, 676–690 (1963)) | 603 | 21724 |
| *Streptomyces albus* SF-1089 (this strain is coincident with *Streptomyces albus* as described in Waksman's "The Actinomycetes" vol.2 (1961)) | 604 | 21725 |
| *Streptomyces flavus* | 605 | — |
| *Streptomyces aureofaciens* | 606 | — |
| *Streptomyces hygroscopicus* var. *angustomyceies* | 607 | — |

Wherein F.R.I. is an abbreviation of "Fermentation Research Institute," Agency of Industrial Science and Technology of the Ministry of International Trade and Industry of Japan, residing in Inage, Chiba City, Japan and ATCC is that of American Type Culture Collection, Washington D.C. U.S.A.

The production medium used for the cultivation of a strain of the Streptomyces to accumulate the amylase may contain one or more of starch, soluble starch, glucose and corn meal etc., as the carbon sources and one or more of defatted soybean meal, defatted cotton seed meal, wheat embryo, peanut meal, ferma media, fish meal, dried yeast, skimmed milk, casein, malt extract, yeast extract, sodium nitrate and potassium nitrate etc., as the nitrogen sources. In addition, it is possible to use and incorporate in the culture medium one or more of inorganic salts such as potassium dihydrogen phosphate, magnesium sulfate, magnanese sulfate, ferric sulfate and calcium carbonate etc., as well as trace elements in order to promote the growth of the microorganism and to enhance the production of the enzyme, if required.

The process of the cultivation of a strain of the Streptomyces may be carried out in a known manner and under the conventional culturing conditions which are usually employed for the cultivation of Streptomyces. Thus, it is possible to perform either liquid cultivation or solid cultivation to produce and accumulate the amylase in a liquid or solid culture medium. However, liquid cultivation and particularly liquid cultivation under submerged aerobic conditions is most preferred. When one of the above-mentioned strains of the Streptomyces is incubated at a temperature of 25°–37° C and at a pH in the range of a weak acidity to a weak alkalinity under submerged aerobic conditions with aeration and agitation, the production of the amylase reaches a maximum in 3 to 5 days of incubation.

For the recovery of the amylase, the culture medium or culture broth in which the incubation of the Streptomyces has been carried out may be treated in a known manner to separate the amylase therefrom. Thus, the culture broth may be filtered to remove the mycelium cake, and the resulting filtrate may then be treated either through a salting-out technique by adding a water-soluble inorganic salt such as ammonium sulfate etc., or through a precipitation method by adding a water-miscible organic solvent such as ethanol, methanol, isopropanol, acetone etc., or through an adsorption-elution method with an ion-exchange resin etc. In this way, the amylase may be separated from the incubated culture medium. The amylase thus separated may be treated further by spray-drying, hot-air drying, vaccum-drying, freeze-drying or lyophilizing to give a crude powder preparation of the amylase.

An electrophoretically homogeneous and pure preparation of the amylase may be obtained by purifying the above mentioned crude powder preparation in a conventional manner which is known for the purification of enzymes, as described in the French Pat. No. 71-38545.

Properties of the amylase there obtained and purified by the above specified purification method are stated below in detail.

1. ENZYMATIC ACTION

When a pure product of this amylase of *Streptomyces hygroscopicus* is reacted with starch and amylose, respectively, these carbohydrates are efficiently hydrolysed, producing a small amount of glucose but a considerably larger amount of maltose are shown below in Table 1.

Table I

| Substrate | Degree of hydrolysis* | Relative amount of sugar products** | | |
|---|---|---|---|---|
| | | Glucose | Maltose | Malto-oligosugars |
| Starch | 74.8% | 3.2% | 58.2% | 38.6% |
| Amylose | 78.6% | 0 | 62.8% | 34.9% |

Referring to Table 1 it is noted that:

* "Degree of hydrolysis" was determined by reacting the amylase with the substrate at pH 5.5–5.8 at 50° C for 20 hours at a substrate concentration of 1% (the amylase being dosed at 500 saccharifying units per 1 g. of the substrate), measuring the total amount of the produced reducing sugars by the Somogyi's titration method, calculating the determined total amount of the reducing sugars as maltose and then evaluating the "degree of hydrolysis" by the following equation:

$$\text{"Degree of hydrolysis"} = \frac{\text{(Total amount of the produced reducing sugars calculated as maltose)}}{\text{(Amount of starch calculated as maltose)}} \times 100$$

where "Amount of starch calculated as maltose" is determined by hydrolysing completely the substrate by heating together with a sufficient quantity of 2N hydrochloric acid in a boiling water bath, neutralising the reaction mixture with sodium hydroxide, measuring the amount of the produced glucose according to the Somogyi's titration method and then calculating the measured amount of the glucose as maltose, that is to say, evaluating a product of the measured amount of the glucose by 0.95 as "Amount of starch calculated as maltose."

Further, in the above Table I, it is noted that:

** "Relative amounts of sugar products" was measured by fractionating the hydrolysed products of the substrate by chromatography, determining separately the quantity of each of the isolated sugar components and expressing the proportions of them in terms of per cent by weight.

2. SUBSTRATE SPECIFICITY.

When a purified preparation of the amylase of Streptomyces hygroscopicus is reacted with various substrates as indicated below, in Table II Table II

| Substrates | Degree of saccharification* | Sugars produced** | | | | |
|---|---|---|---|---|---|---|
| | | $G_1$ | $G_2$ | $G_3$ | $G_4$ | $G_5$ |
| Soluble starch | 100% | ± | +++ | ++ | + | + |
| Maize starch | 92.8% | ± | +++ | ++ | ± | + |
| Glycogen | 45.8% | − | +++ | ++ | ± | ± |
| Amylose | 106.5% | − | +++ | ++ | − | + |
| Dextrin | 91.0% | ± | +++ | ++ | ± | + |
| β-Cyclodextrin | | − | − | − | − | ± |

Table II-continued

| Substrates | Degree of saccharification* | Sugars produced** | | | | |
|---|---|---|---|---|---|---|
| | | $G_1$ | $G_2$ | $G_3$ | $G_4$ | $G_5$ |
| α-Cyclodextrin | | − | + | − | − | ± |
| Maltohexaose | | − | ++ | + | + | − |
| Maltopentaose | | − | ++ | ++ | − | |
| Maltotetraose | | ± | ++ | ± | | |
| Maltotriose | | − | − | | | |
| Maltose | | − | | | | |
| Phenyl α-D-glucoside | | − | | | | |

Referring to Table II it is noted that:

* "Degree of saccharification" was determined by such a scale that the "degree of hydrolysis" of soluble starch by the action of a given amount of the purified amylase is assumed as 100%.

** "Sugars produced" were analyzed by detecting the presence of the respective sugars by a paper chromatography after reacting the enzyme with the substrate of a pH value of 5.5 at a substrate concentration of 0.8% and at an enzyme concentration of 0.00017% at 40° C for 60 minutes.

In the above Table II, the letters $G_1$, $G_2$, $G_3$, $G_4$ and $G_5$ indicate glucose, maltose, maltotriose, maltotetraose and maltopentaose, respectively. The scales have the following significances:

| | | |
|---|---|---|
| +++ | : | A very large amount of the sugar is present. |
| ++ | : | A large amount of the sugar is present. |
| + | : | A significant amount of the sugar is present. |
| ± | : | A trace of the sugar is present, and |
| − | : | No presence of the sugar is detectable. |

The amylase of the present invention was reacted in a similar way with the other substrate glucan such as laminaran (araban β-1,3:β-1,6=7:3), pachyman (β-1,3) and dextran (available as Sephadex G-100, α-1,6), and it was then found that these glucan could not be hydrolysed by the action of the amylase of the present invention.

3. Optimum pH, stable pH and other properties.

The new, pure amylase of *Streptomyces hygroscopicus* exhibits optimum pH, pH stability, optimum temperature and thermal stability, molecular weight and other enzyme-chemical and physical and chemical properties as summarised in Table III below,

TABLE III

| Properties | Value |
|---|---|
| Optimum pH for activity | 4.5–5.0 |
| Optimum temperature for activity | 50–60° C |
| pH stability | Residual enzymatic activity is no less than 90% of the initial activity after the enzyme is treated at 40° C for 60 minutes at pH of 4.5–9.8. |
| Thermal stability | Residual enzymatic activity is no less than 50% after the enzyme is treated at pH of 6.8 at a 30° C–95° C for 15 minutes. |
| Specific activity | Liquefying potency : 23100 μ/mg. N Saccharifying potency : 59600 μ/mg. N |
| Elementary analysis | C 44.87%, H 6.84%, |

TABLE III-continued

| Properties | Value |
|---|---|
| | N 13.84% |
| Molecular weight | ca. 35,000 (as determined by the gel-filtration method) |
| Ultraviolet absorption | $E_{1\,cm}^{1\%}$ = 13.1, at 280mμ (pH = 6.8) |
| Isoelectric point | About pH 4.3 (measured by the isoelectric point electrophoresis) |
| Electrophoresis (in cellulose acetate gel) | Migration of 2.2 cm towards the positive pole for 65 minutes by an electric current of 0.8 mA/cm., buffered at pH 8.7 by Tris hydrochloric acid buffer solution ($\mu$ = 0.05). |

DETAILED DESCRIPTION OF THE INVENTION

The present invention is based on the discovery of a process in which a liquefied starch is reacted with β-amylase to degrade the chains of the amylose and amylopectin constituting a starch molecule, and then the streptomyces amylase is added to further hydrolyze the remaining chains. However, the reaction procedure can be effected even though β-amylase and streptomyces amylase have been permitted to coexist in an adequate amount of each amylase, because of the difference in reaction velocity between both amylases, therefore the stretomyces amylase can be added simultaneously with the β-amylase or during reaction of β-amylase. Furthermore, where highly branched starch is used as the substrate, it is expected that employment of isoamylase together with the above enzymes efficiently carries out the saccharification of the starch.

The present invention will be described concretely by a process in which maltose is produced according to the action of the above mentioned streptomyces amylase following the treatment with β-amylase.

Starch must be liquefied prior to the action of β-amylase. As the starch materials, those used commonly for the production of starch hydrolyzate, such as corn starch, potato starch, sweet potato starch, tapioca starch, rice starch, wheat starch, and their α-inverted ones are available for use in this invention. As the procedure for liquefaction, a mechanical process accompanied with heating as well as conventional enzumatic processes using α-amylase or the streptomyces amylase are available.

At the liquefaction step, the extent of the degradation of the chain of the starch molecule is desirably small. Generally, the value of DE is favorably less than 4, though a value below 10 does not deviate from the purpose of the present invention.

After liquefaction, the above mentioned liquified solution is cooled to the temperature range in which β-amylase can react actively, e.g. 45°–65° C, then the pH is adjusted to the range of 4.5 – 6.0, and β-amylase is added. The reaction period is dependent on the amount of the enzyme used, the reaction temperature, and the reaction pH.

The action of β-amylase may either be allowed to proceed to its maximum extent for degradation of it may be stopped a little before it. The content of maltose at this step is generally around 60%.

Next, the degradation of starch in the solution is further progressed by addition of the streptomyces amylase. At this step, β-amylase in the solution may either be inactivated prior to the addition of the streptomyces amylase or be left as it is. The appropriate amount of the streptomyces amylase added is generally 200–1500 units/g starch, and the reaction temperature and pH are kept at 45°–65° C and 5.0 – 7.0, respectively.

Units of activity of the above mentioned enzyme are determined as follows: A mixture composed of 1 ml of enzyme solution, 2 ml of 2% soluble starch solution and 2 ml of McIlvaine buffer of pH 5.5, was incubated at 40° C for 3 minutes. The reaction was stopped by adding 1 ml of the reaction mixture into Somogyi's reagent. The amount of the produced reducing sugars is determined by the Somogyi's titration method, and the measured amount of the reducing sugars produced is calculated as maltose in the whole 5 ml of the reaction mixture. One unit is designated as the amount of the enzyme capable of producing 1 mg of maltose in 60 minutes.

A practical period for saccharification is within 72 hours in total and the content of maltose in the solution at this step is 80 – 90%. After the completion of saccharification, the solution is decolorized and purified using active carbon and ion exchange resin and concentrated to the prescribed concentration according to the conventional method to obtain a final product.

EXAMPLE 1

Six Kg of sweet potato starch containing 16% of water was suspended in 11 l of water, the pH of which was adjusted to 6.0, and the starch was liquified according to a liquifaction process at 87° C with 10 units/g starch of a bacterial liquifying amylase. The value of DE Dextrose equivalent after inactivation of the α-amylase by boiling was 3.6. The resulting solution was cooled at 55° C, and saccharified for 4 hours by addition of 15 units/g starch of β-amylase. Afterward the partially saccharified solution was boiled for the purpose of inactivating β-amylase, and then cooled at 55° C. The streptomyces amylase amount to 1200 units/g starch was added while maintaining the pH of the solution at 6.0, and the saccharification was proceeded for 70 hours in total.

After completion of the reaction, the solution was boiled, filtrated, and decolorized and purified with active carbon and ion-exchange resin. The sugar composition of the product determined quantitatively with gas liquid chromatography was as follows:

| Procedure | Sugar composition (%) | | |
|---|---|---|---|
| | Glucose | Maltose | Maltotriose |
| Process according to Example 1 | 7.2 | 83.6 | 4.8 |

| Procedure | Sugar composition (%) | | |
|---|---|---|---|
| | Glucose | Maltose | Maltotriose |
| (15 units of β-amylase plus 1200 units of the streptomyces amylase) Control (1500 units of the streptomyces amylase alone) | 9.4 | 76.4 | 8.8 |

EXAMPLE 2

One hundred Kg of potato starch containing 18% of water was made up to a 30% aqueous suspension, adjusted to pH 6.0, and liquefied by liquifaction process at 85° C with 200 units/g starch of the streptomyces amylase.

The resulting liquified solution was steamed for inactivating the amylase, cooled at 65° C, and saccharified for about 2 hours at pH 6.0 with 15 units/g starch of β-amylase to obtain a saccharified solution consisted of maltose 62.0%, maltotriose 0.3%, and limit dextrin 37.7%. The solution was cooled to 55° C, added with 1500 units/g starch of the streptomyces amylase, and further saccharified for 48 hours while maintaining the pH at 6.0. The resulting solution was decolorized and purified according to the conventional method, and concentrated at 75% to obtain the final product.

According to a gas liquid chromatographic analysis, the sugar composition of the product was glucose 8.0%, maltose 84.5%, and maltotriose 5.0%.

EXAMPLE 3

1.4 Kg of corn starch was suspended in 1.5 l of tap water, to which bacterial liquifying amylase and calcium hydroxide corresponding to 0.3% and 0.02% of the starch used, respectively, were added. The solution was adjusted to pH 6.0 and poured into 1.3 l of hot water at the temperature of 90°–91° C prepared separately to undergo the primary liquifaction. Then, the solution was heated at 120° C for 10 minutes, and liquefied again by addition of 0.05% of bacterial liquifying amylase. After the completion of enzyme reaction, the solution was heated at 100° C for 5 minutes for inactivating the amylase, and cooled to 55° C. Saccharification was conducted for 4 hours by addition of β-amylase in an amount corresponding to 0.2% of the starch used, and followed by 800 units/g starch of the streptomyces amylase to complete the saccharification in 72 hours totally. The solution was decolorized and purified according to the conventional method, and concentrated to 75% to obtain the final product. The analytical value of the product was glucose 4.3, maltose 80.2%, and maltotriose 9.5%.

The streptomyces enzyme used in the above mentioned Examples 1 – 3 was the one produced by *Streptomyces hygroscopicus* and prepared as follows: 100 ml of a seed medium composed of corn meal 2%, wheat embryo 1%, and ferma media 0.5%, pH 7.0, was put into a 500 ml volume flask and sterilized. Spores or mycelia of *Streptomyces hygroscopicus* were inoculated in it and cultivated at 28° C for 24 hours with shaking, to give a seed culture. 20 l of a production medium composed of soluble starch 12%, soybean meal 3%, and potassium dihydrogen phosphate 0.2%, pH 7.0, was in a 30 liter-volume jar fermentor was sterilized, and then cooled, to which the above mentioned seed culture was transferred and cultivated at 35° C for 90 hours. The filtrate of the resulting culture broth was concentrated to 1/5 of the initial volume, and added with twice volume of cold ethanol to precipitate the enzyme. 77 g of the crude enzyme preparation corresponding to 45,000 units per gram was obtained from the precipitate after drying.

EXAMPLE 4

Example 3 was repeated excepted that the saccharification temperature was 60° C and the time was 48 hours. The product was composed of glucose 4.2%, maltose 81.4%, and maltotriose 9.2%.

EXAMPLE 5

Instead of the purified preparation of the enzyme produced by *Streptomyces hygroscopicus* used in the example 4, a preparation of the enzyme produced by *Streptomyces tosaensis nov. Sp* was used for saccharification to obtain a product composed of glucose 4.5%, maltose 80.6%, and maltotriose 9.4%. The enzyme produced by *Streptomyces tosaensis nov. Sp* was prepared as follows: Spores or mycelia of *Streptomyces tosaensis nov. Sp* were inculated in 100 ml of a seed medium composed of corn meal 2%, wheat embryo 1%, and ferma media 0.5%, at a pH of 7.0, in a 500 ml volume shaking flask and cultivated at 28° C for 24 hours with aeration and agitation. The resulting seed culture was transferred to 20 l of a production medium composed of corn meal 8.4%, polypeptone 2%, and potassium dihydrogen phosphate 0.2%, pH 7.0, and cultivated at 28° C for 85 hours with aeration and agitation. The filtrate of the culture broth thus obtained was concentrated at below 40° C under reduced pressure to 1/5 of the initial volume and added with twice volume of cold ethanol. The precipitated amylase was dried up to obtain 28 g of the crude preparation corresponding to 22,000 units per gram.

EXAMPLE 6

Instead of the purified preparation of the enzyme produced by *Streptomyces hygroscopicus* used in the example 4, a preparation of the enzyme produced by *Streptomyces albus* was used for saccharification, resulting in a product composed of glucose 3.9%, maltose 81.0%, and maltotriose 9.0. The enzyme produced by *Streptomyces albus* was prepared as follows: 100 ml of a seed medium composed of corn meal 2%, wheat embryo 1%, and ferma media 0.5%, pH 7.0, was put into a 500 ml volume shaking flask and sterilized, wherein spores or mycelia of *Streptomyces albus* were inoculated and cultivated at 28° C for 24 hours with shaking to obtain a seed culture. 20 l of a production medium composed of soluble starch 9.4%, fish powder 1.3%, and potassium dihydrogen phosphate 0.2%, pH 7.0, was put into a 30 l volume jar fermentor, sterilized, and cooled, to which the above mentioned seed culture was transferred and cultivated at 35° C for 90 hours. The filtrate of the resulting culture broth was concentrated to 1/5 of the initial volume and added with twice volume of cold ethanol to precipitate the amylase. 53 g of a crude preparation of the enzyme corresonding to 10,000 units per gram was obtained from the precipitate after drying.

What is claimed is:

1. A process for the production of maltose from a liquified starch having a DE of not more than 10, which comprises saccharifying said liuqified starch at a temperature from about 45° C to about 65° C and at a pH of from about 4.5 to 7.0 with a β-amylase and a new Streptomyces amylase produced by a strain of the species Streptomyces selected from the group consisting of *Streptomyces hygroscopicus, Streptomyces virido chromogenes, Streptomyces aureofaciens, Streptomyces flavus, Streptomyces hygroscopicus* vs. *angustomyces, Streptomyces albus, Streptomyces tosaensis nov. Sp.* at the same time or separately.

2. Process according to claim 1, wherein said liquified starch is a starch which is prepared from a member selected from the group consisting of potato starch, corn starch, sweet potato starch, tapioca starch, wheat starch, rice starch, the α-starch of any said starches, and a mixture of at least two of said starches.

3. Process according to claim 2, wherein said streptomyces is *Streptomyces hygroscopicus* and the DE value of said liquified starch is below 10.

4. Process according to claim 2, wherein said streptomyces is *Streptomyces tosaensis nov. Sp.* and the DE value of said liquified starch is 10.

5. Process according to claim 2, wherein said streptomyces is *Streptomyces albus* and the DE value of said liquified starch is below 10.

6. Process according to claim 2, wherein said streptomyces is *Streptomyces hygroscopicus*.

7. Process according to claim 2, wherein said streptomyces is *Streptomyces tosaensis nov. Sp.*

8. Process according to claim 2, wherein said streptomyces is *Streptomyces albus*.

9. Process for the production of maltose, according to claim 2, wherein said liquefied starch is saccharified with β-amylase and then with 200 to 1500 units/g starch of said streptomyces amylase.

10. Process according to claim 2, wherein said saccharification is carried out by β-amylase at pH about 4.5 to 6.0 and by said streptomyces amylase at ph about 5.0 to 7.0, and the total reaction time is within 72 hours.

11. Process according to claim 10, wherein the DE value of said liquefied starch ranges from below between about 10 to about 4.

12. Process according to claim 1, wherein the liquefied starch is saccharified by the use of β-amylase and said streptomyces amylase simultaneously, the amount of said streptomyces amylase being about 200 to about 1500 units/g of said starch.

13. Process according to claim 1, wherein the saccharifying is carried out at a temperature from about 45° C to 65° C and at a pH from about 4.5 to 7.0 within 72 hours.

14. Process according to claim 13, wherein the saccharifying is carried out at a pH of from about 5.0 to 6.0.

15. Process according to claim 12, wherein the DE value of said liquified starch is below 10.

16. Process according to claim 12, wherein the DE value of said liquified starch is below 4.

17. Process for the production of maltose, according to claim 1, wherein said liquefied starch is saccharified with β-amylase, and then with 200 to 1500 units/g starch of said streptomyces amylase.

* * * * *